United States Patent
Guo et al.

[11] Patent Number: 5,938,909
[45] Date of Patent: Aug. 17, 1999

[54] CUP-SHAPED VERTICAL SLAB GEL ELECTROPHORESIS APPARATUS

[76] Inventors: Rong Guo; Qi-Feng Ma, both of 28271 Trailriders Dr., Rancho Palos Verdes, Calif. 90275

[21] Appl. No.: 08/818,254

[22] Filed: Mar. 14, 1997

Related U.S. Application Data

[60] Provisional application No. 60/013,442, Mar. 15, 1996.

[51] Int. Cl.[6] ................................................. G01N 27/26
[52] U.S. Cl. ............................................................. 204/619
[58] Field of Search .................................... 204/465, 466, 204/467, 456, 606, 615, 616, 617, 618, 619, 620

[56] References Cited

U.S. PATENT DOCUMENTS

| | | | |
|---|---|---|---|
| 3,932,263 | 1/1976 | Brefka | 204/607 |
| 4,574,040 | 3/1986 | Delony et al. | 204/606 |
| 4,588,491 | 5/1986 | Kreisher et al. | 204/620 |
| 4,729,823 | 3/1988 | Guevara, Jr. | 204/621 |
| 5,525,202 | 6/1996 | Evans et al. | 204/606 |

OTHER PUBLICATIONS

J. Hejgaard, Cylindrical Slab Gel Electrophoresis in a Single Tank. Analytical Biochemistry vol. 90, 832–834 (1978).
Junichi Akiyama, Cylindrical Stationary Phase Electrophoresis Apparatus. Chemical Abstract vol. 110, 72141j (1989).
William C. Black IV, et al., Vertical Slab Gel Electrophoresis on a large Number of Samples. Analytical Biochemistry vol.138 210–216 (1984).
Kazuo Yoshida, A Highly Simplified Horizontal Electrophoretic Apparatus . . . Analytical Biochemistry, vol. 130, 246–259 (1983).
Branko Kozulic, Looking at Bands from Another Side. Analytical Biochemistry vol. 216, 253–261 (1994).
Michael Albin, et al., Sensitivity Enhancement for Capillary Electrophoresis. Analytical Chemistry vol. 65, 489A–497A (1993).

*Primary Examiner*—Robert Warden
*Assistant Examiner*—Alex Noguerda

[57] ABSTRACT

The titled apparatus mainly comprises an outer casting member having a hollow frustum channel lined detachably by a flexible sheet, an inner casting member having an exterior lateral wall of frustum shape being placed within the sheet-lined channel of the outer casting member, a gel slab sandwiched concentrically in the space between the interior wall of the sheet-lined channel and the exterior lateral wall of the inner casting member, and a method to expose the entire gel by first slipping off the outer casting member from the flexible sheet, then peeling off the flexible sheet from the gel slab, and then taking the entire gel slab off from the inner casting member. The apparatus provides a vertical electrophoresis means for both agarose gel electrophoresis and polyacrylamide gel electrophoresis with the advantages of large sample capacity, higher sensitivity, short analysis time, and simple operation.

13 Claims, 3 Drawing Sheets

CUP-SHAPED VERTICAL SLAB GEL ELECTROPHORESIS APPARATUS

This application claims benefit of Provisional Appl. 60/013,442 filed Mar. 15, 1996.

FIELD OF THE INVENTION

The invention relates to vertical slab gel electrophoresis, more specifically, to an apparatus for preparation and electrophoresis of a vertical gel slab of hollow frustum shape.

BACKGROUND OF THE INVENTION

Gel electrophoresis is used to separate proteins and nucleic acids and is one of the most important tools in modern biotechnology. It consists of gel, buffer, and electrodes. Samples are loaded in the gel, electric current is applied to the gel through the buffer from the electrodes, and the samples are separated in the gel according to their mobility difference in electric field. Based on its geometry, gel electrophoresis can be classified as capillary gel electrophoresis, column gel electrophoresis, and slab gel electrophoresis. Slab gel electrophoresis is most widely used among them.

Slab gel electrophoresis utilizes a gel slab as separation media and the gel slab should be separated from its casting mold after electrophoresis for analysis. It is convenient, economic, and simple. Multiple samples can be analyzed at the same time and results can be visualized directly. Slab gel electrophoresis includes two major types, horizontal slab gel electrophoresis and vertical slab gel electrophoresis.

Most agarose gel slabs are horizontal type and are used for analysis of nucleic acids. A horizontal agarose gel slab is prepared in a tray with a flat bottom. Hot agarose solution is poured into the tray and a comb is placed on the tray with its teeth extending in the solution but not touching the bottom of the tray. After the agarose solution solidifies, the comb is removed to leave wells for loading samples. The gel slab is then submerged in a buffer, samples are loaded into the wells, and electric current is applied onto the gel slab to separate the samples. After electrophoresis the gel slab is stained and the sample bands are visualized and photographed.

Horizontal agarose gel electrophoresis becomes an indispensable tool in molecular biology. The agarose gel separates nucleic acids according to size difference with a wide separation range (from dozens of base pairs to millions of base pairs). The slab geometry allows simultaneous analysis of multiple samples. The horizontal format provides a very simple procedure for gel preparation. Horizontal agarose gel electrophoresis is used in gene mapping, library screening, southern/northern blotting, and other researches related to nucleic acid analysis.

Horizontal agarose gel electrophoresis also has some unavoidable disadvantages. Submerging an agarose gel slab in a buffer provides good heat exchange between the gel slab and the buffer, but it also increases the cross section of electric field during electrophoresis, generating high electric current which prevents applying high voltage onto the gel slab. Since mobility of samples in a gel slab is proportional to voltage applied, horizontal slab gel electrophoresis needs long time to complete. Submerging an agarose gel slab in a buffer also prevents from using thin agarose gel slabs because samples in thin gel slabs will easily diffuse into the surrounding buffer and decreases detection sensitivity. The way of forming sample wells on a horizontal agarose gel slab also requires thick gel slab since the bottom of sample wells should be a gel layer of certain thickness to prevent samples from leaking. Sample wells should also be deep enough to load certain volume of samples. Practically, the thickness for a horizontal agarose gel slab is about 5 millimeter.

The thickness of the gel slab adds more disadvantages to horizontal agarose gel electrophoresis. It wastes expensive agarose. It dilutes samples, decreasing sensitivity. It slows down staining/destaining process, increasing analysis time. As a gel slab becomes thick, electric field on the cross section of the gel slab is not uniform which results in band-bending, a major factor for inferior resolution for horizontal agarose gel electrophoresis. It is more problematic for blotting process since a thick gel often results in smear bands and also requires long blotting time.

The submerging nature of a horizontal gel slab prevents it from application of isotachophoresis, a technique used in capillary zone electrophoresis for sample concentration. The technique can increase detection sensitivity by 1 to 2 order of magnitude, making the detection of low abundant components in the sample possible. However, the technology requires the sample loading side and its opposing side of the separating media expose to two different buffers. In horizontal agarose gel electrophoresis, the gel slab is submerged in a single buffer, restricting application of isotachophoresis. In another words, horizontal agarose gel electrophoresis cannot detect low abundant components, greatly downgrading its usefulness.

Contrary to the horizontal agarose gel slab which is free from casting mold during electrophoresis, a vertical gel slab is cast in a detachable cassette which remains integrated with the gel slab during electrophoresis. The detachable cassette consists of two plates, a comb of multiple teeth, and a pair of spacers the two spacers are held between the two plates along the two vertical edges of the two plates, forming a cassette with a rectangular interstice. The bottom of the cassette is detachably sealed and a gelable solution is added into the interstice from its top opening. The comb is placed on the top of the cassette with its teeth extending into the gelable solution. After the gelable solution solidifies, the comb is removed to generate sample wells. The gel-containing cassette is clamped onto a vertical electrophoresis device with the sample loading end and its opposing end exposing to two separate buffer chambers for electrophoresis.

Most of vertical gel slabs are polyacrylamide type and are mainly used for protein analysis and DNA sequencing. The vertical gel slab is protected within the cassette and its two ends expose to two different buffer chambers. Though not reported previously, this configuration allows applying isotachophoresis on the gel to concentrate samples. The vertical cassette format allows preparation of a very thin gel slab for electrophoresis. The thin gel slab provides good heat exchange and has low electric current due to smaller cross-section of electric field so that high voltage can be applied on it to decrease analysis time. The thin gel slab minimizes sample diffusion and results in good resolution. The thin gel slab increases productivity by shortening staining/destaining process. The thin gel slab also saves expensive gel materials. However, an agarose gel slab cannot be easily and effectively prepared in thin vertical format. Most biochemistry laboratories have to keep both horizontal electrophoresis apparatus for agarose gel and vertical electrophoresis apparatus for polyacrylamide gel.

Many factors prevent from preparation of cassette-type vertical agarose gel slabs. To prepare a cassette-type vertical agarose gel slab, hot agarose solution should be added into the narrow cassette interstice. The gel solution solidifies in the cassette when it cools down. Unfortunately, the gel also shrinks during cooling, a severe problem for preparation of a vertical agarose gel slab. Gel shrinkage makes the gel slab thinner and generates void between the cassette plates and the gel slab. A component in a sample travels both in the gel slab and in the void with different mobility, resulting in band diffusion. The cassette has less contact with the thinner gel slab which often slips off from the cassette during electrophoresis gel shrinkage also results in unpredictable gel break. Lowering temperature of agarose solution will reduce the degree of shrinkage. But in this way, the agarose solution will solidify before it reaches the bottom of the interstice generating air bubbles which ruins the gel slab. An agarose gel slab is tender than a polyacrylamide gel slab and deforms when it is clamped onto a vertical electrophoresis apparatus. In general, vertical agarose gel electrophoresis is impractical in the currently available vertical gel electrophoresis systems.

Besides that it is not suitable for agarose gel electrophoresis, the conventional vertical gel electrophoresis system also has other limitations. Since the gel cassette is installed for electrophoresis by clamping its two vertical sides onto an electrophoresis device, the cassette plates have to be thick enough so that they will not bend horizontally by clamping. When a wider cassette is used for loading more samples, thicker plates have to be selected to avoid horizontal bending, which slows down heat exchange. Sample loading capacity is restricted by this factor. Conventional plates for vertical gel electrophoresis are 1 millimeter thick and 80 millimeter wide for mini-gels and 3 millimeter thick and about 300 millimeter wide for sequencing gels.

The spacers on the two vertical sides of the cassette often affect uniformity of the electric field in a vertical gel slab. The sides and the mid-portion of the cassette usually subject to different voltage drop which generates uneven migration of sample bands called "smiling effect". This effect will be maximized by insufficient heat exchange. Smiling effect will affect the quality of electrophoresis and some times makes identification of adjacent bands difficult.

As the size of a cassette increases, preparation of a gel slab in the cassette turns to be difficult. For example, to prepare a DNA sequencing gel slab of 0.1 to 0.4 millimeter thickness in a vertical cassette is very difficult and often fails due to air bubbles generated during addition of the gelable solution. To separate the gel slab from the casting plates is also troublesome and the gel slab often breaks during this process. For this reason, a toxic silanization reagent is spread onto one plate to help the separation of the gel slab from the casting plates. Besides exposure to toxic material, this process can not completely prevent the gel slab from break and skillful workers are still required.

J. Hejgaard reported a hollow cylindrical gel slab for vertical gel electrophoresis the casting mold comprises hollow cylinders A and B. The internal diameter of cylinder A is slightly larger than the outer diameter of cylinder B so that an interstice forms between the two cylinders when cylinder B is inserted into cylinder A. A gel slab forms in the interstice. Although a hollow cylindrical gel slab of 2.5 millimeter thickness was prepared, it has never become practical due to its messy and awkward operation. Unlike the cassette-type vertical gel format in which plates are removed from the gel slab by lifting, one has to pull one cylinder away from the other to expose the gel and the gel slab with the thickness of 1 millimeter or less is unavoidably damaged.

In general, further advancement in slab gel electrophoresis is needed to overcome the limitations of the conventional technologies. There is a need to develop a vertical agarose gel electrophoresis system so that isotachophoresis technique can be applied to agarose gel slabs for higher sensitivity. There is a need to prepare thinner agarose gel for better resolution, shorter analysis time, and lower material consumption. There is a need to increase loading capacity of the current cassette-type vertical gel electrophoresis system without slowing down heat exchange and increasing the physical size of the system. There is a need to overcome the ununiform electric field across the cassette-type vertical gel slab so that smiling effect can be eliminated and better results obtained. There is a need to further simplify the process of vertical slab gel electrophoresis.

SUMMARY OF THE INVENTION

The present invention relates to vertical slab gel electrophoresis. Unlike the conventional vertical slab gel electrophoresis where a gel slab is sandwiched between two plates, the gel slab of the present invention is sandwiched between two concentrically-assembled casting members of hollow frustum shape. The outer casting member has a hollow frustum channel lined detachably by a flexible sheet the narrow end of the sheet-lined channel is detachably sealed, forming a cup-shaped cavity. The inner casting member is a frustum having a cavity on its wide end, a bottom on its narrow end, and an exterior lateral wall resembling the interior lateral wall of the cup-shaped cavity by shape but smaller than it by size. To prepare a gel slab, a gelable solution is added in the cup-shaped cavity, the inner casting member is placed within the cup-shaped cavity to squeeze the gelable solution into the space between the interior lateral wall of the cup-shaped cavity and the exterior lateral wall of the inner casting member, and a circular comb member with multiple teeth is placed at the opening of the cup-shaped cavity with its teeth extending into the gelable solution. After the gel slab forms, the comb member is removed to leave a first gel exposure with many wells. The detachable seal on the narrow end of the outer casting member is also removed to leave a second gel exposure. The remaining components forms a gel assembly of frustum shape. The gel assembly has a second gel exposure on its narrow end and a first buffer chamber which includes the top portion of the cup-shaped cavity and the cavity of the inner casting member with the first gel exposure at their junction. The gel assembly is placed in a second buffer chamber containing a second buffer and a fixed electrode with the second gel exposure submerging in the buffer. A first buffer and a movable electrode is placed in the first buffer chamber with the first gel exposure covered by the buffer. Samples are loaded into the wells on the first gel exposure and electric current is applied onto the gel slab by the two electrodes. After electrophoresis, the gel slab is separated from the casting components by slipping off the outer casting member from the flexible sheet, peeling off the flexible sheet from the gel slab, and lifting off the gel slab from the inner casting member. The gel slab is now ready for staining and analysis.

One objective of the present invention is to provide a device for vertical agarose gel electrophoresis so that samples can be concentrated to increase sensitivity and thin agarose gel slabs can be prepared for better resolution and shorter analysis time.

Another objective is to provide a device which can be used for both agarose slab gel electrophoresis and polyacrylamide slab gel electrophoresis.

Another objective is to expand sample loading capacity of vertical slab gels without increasing the physical size of its corresponding device.

Another objective is to eliminate ununiform electric field in the conventional cassette-type vertical gel slab during electrophoresis.

Another objective is to simplify the process of vertical slab gel electrophoresis.

DETAILED DESCRIPTION OF THE PREFERRED EMBODIMENT

Figure 1:
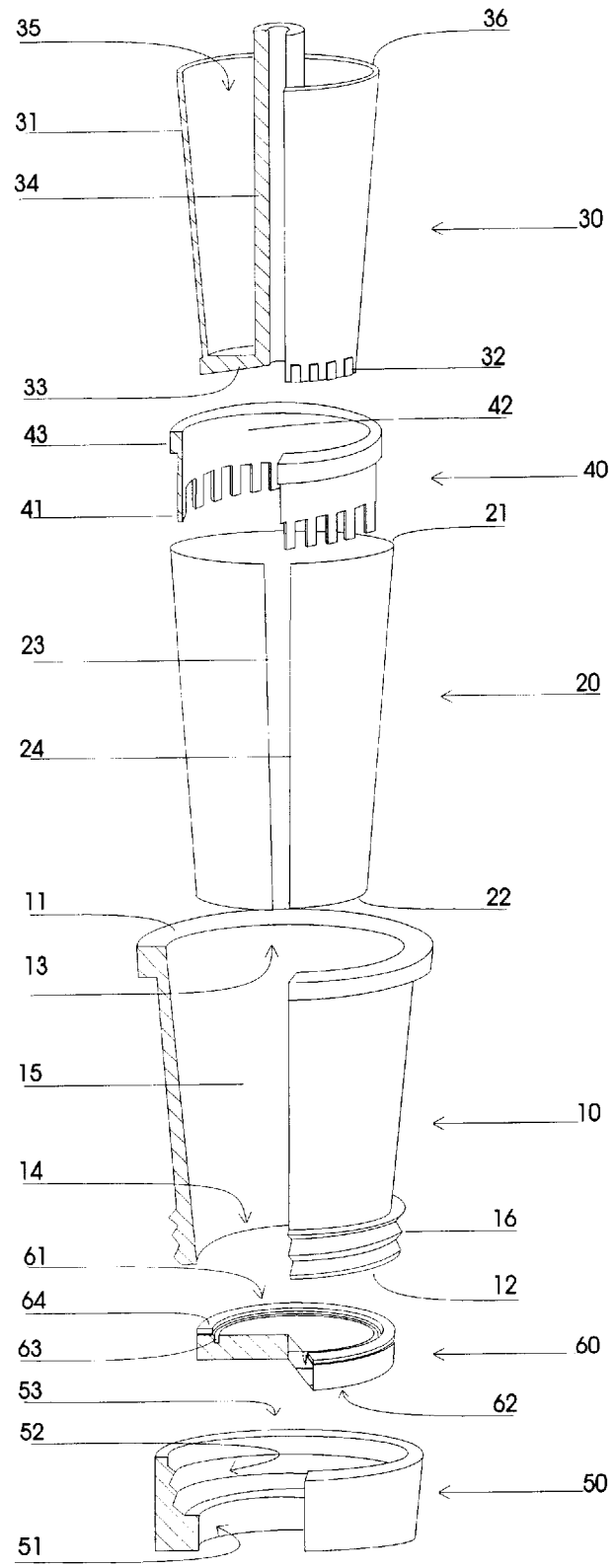
FIG. 1 is an exploded view of the gel casting apparatus before assembling.
Figure 3:
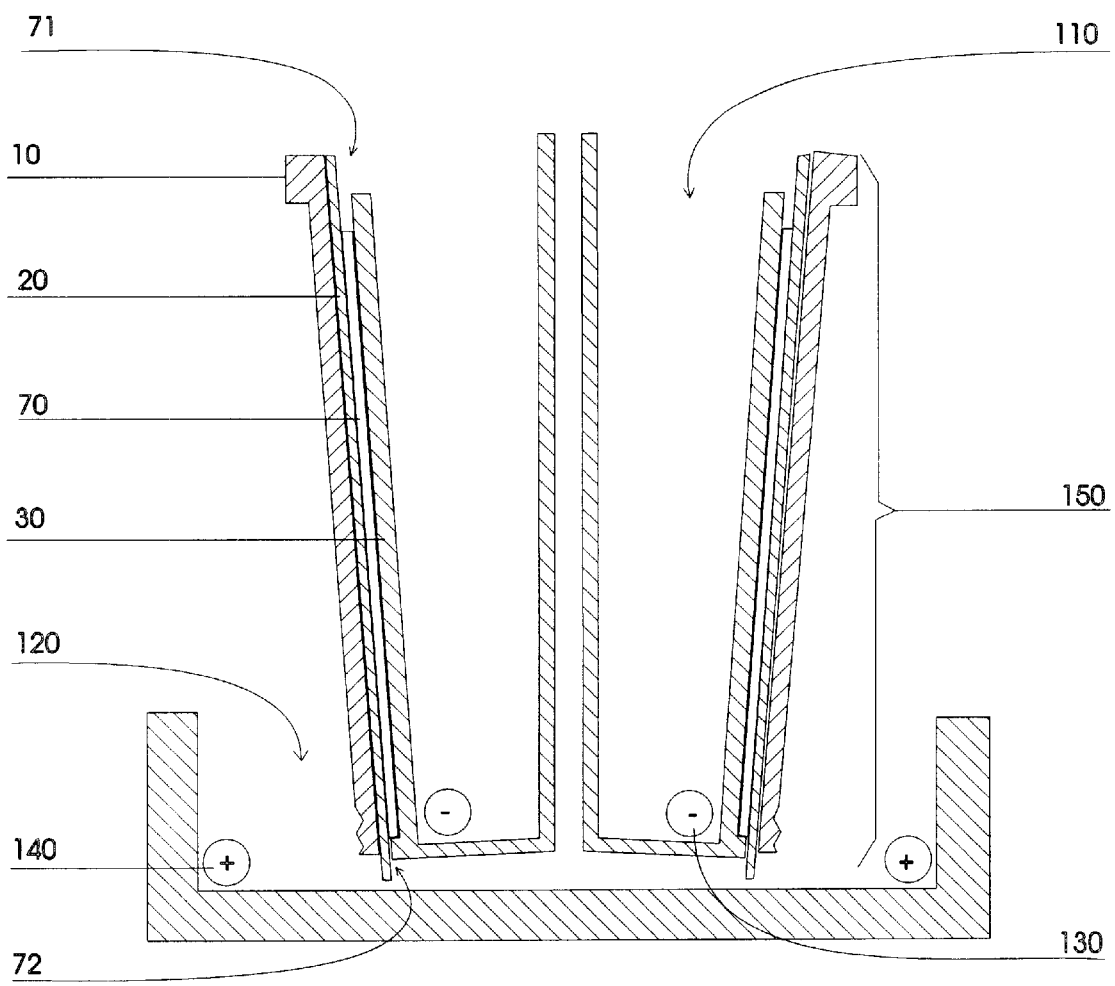
FIG. 3 is a cross-sectional view of the electrophoresis system in accordance with the present invention.

Referring to FIGS. 1 and 3, the preferred embodiment of the present invention comprises outer casting member 10, flexible sheet 20, inner casting member 30, comb member 40, screw member 50, disc member 60, gel 70, first buffer chamber 110, second buffer chamber 120, movable electrode 130, and fixed electrode 140. Outer casting member 10 is a hollow frustum made of non-conductive material with good mechanical strength. It has wide end 11, narrow end 12, first opening 13 at said wide end, second opening 14 at said narrow end, channel 15, and male threaded portion 16. Channel 15 has a decreased diameter from first opening 13 to second opening 14. Male threaded portion 16 is mounted on the exterior wall at narrow end 12 of outer casting member 10. Flexible sheet 20 is a longitudinally-cut hollow frustum made of flexible non-conductive material. It has even thickness of less than 1 millimeter and comprises top side 21, bottom side 22, left vertical side 23 and right vertical side 24. Top side 21 of flexible sheet 20 has a diameter the same as that of first opening 13 of outer casting member 10 and the lateral structure of flexible sheet 20 shares the same frustum angle as that of channel 15 of outer casting member 10. The frustum structure of flexible sheet 20 is a few millimeters higher than the frustum structure of channel 15 of outer casting member 10. Inner casting member 30 comprises lateral wall 31, base slot 32, bottom 33, hollow stem 34, cavity 35, and top 36. The exterior structure of lateral wall 31 has the same geometrical shape as channel 15 of outer casting member 10 but shorter and narrower than the channel. It is constructed in such a way that when inner casting member 30 is concentrically placed within channel 15 of outer casting member 10 to let bottom 33 of inner casting member 30 level to second opening 14 of outer casting member 10, the exterior of lateral wall 31 and the interior wall of channel 15 are spaced apart evenly all the way up to top 36 of inner casting member 30. A plurality of regularly spaced protrusions distribute along the bottom edge of wall 31, forming base slot 32 which ensures the concentric insertion of inner casting member 30 into outer casting member 10. Bottom 33 seals inner casting member 30 at the bottom edge of wall 31. Bottom 33 preferably has an external concave on its exterior surface and has a hole in the center. Hollow stem 34 is a rigid tubing mounted in the hole of bottom 33. Comb member 40 is a circular strip with a diameter slightly smaller than first opening 13 of outer casting member 10. It consists of teeth 41, base 42, and flange 43. Teeth 41 are a plurality of regularly spaced protrusions on one side of base 42. The thickness of teeth 41 matches the protrusions of base slot 32. Flange 43 locates on the opposing side of teeth 41 and extends laterally a few millimeters. Screw member 50 is a hollow cylinder and consists of rim 51, female threaded portion 52, and cavity 53. Female threaded portion 52 is constructed on the interior surface of the hollow cylinder and matches male threaded portion 16 of outer casting member 10. Rim 51 extends inwardly by a few millimeters from the lateral wall of the hollow cylinder and functions to hold disc member 60 within cavity 53. Disc member 60 is a circular plate and has a diameter the same as the outer diameter of narrow end 12 of outer casting member 10. Disc member 60 has top surface 61 and bottom surface 62. Top surface 61 contains groove 63 and gasket 64. Groove 63 is circular, about 1 millimeter wide and a few millimeter deep, and has the same diameter as that of second opening 14 of outer casting member 10. Gasket 64 locates between groove 63 and the edge of disc member 60 and is made of rubber or plastic. Second buffer chamber 120 is a cavity enclosed by a container of any shape with an opening at the top fixed electrode 140 is installed in second buffer chamber 120 and communicates with a electric source by any means applicable. Movable electrode 130 can be constructed in any shape as long as it can be placed in first buffer chamber 110 and connected to an electric source. First buffer chamber 110 is formed during gel preparation and is described below.

Figure 2:
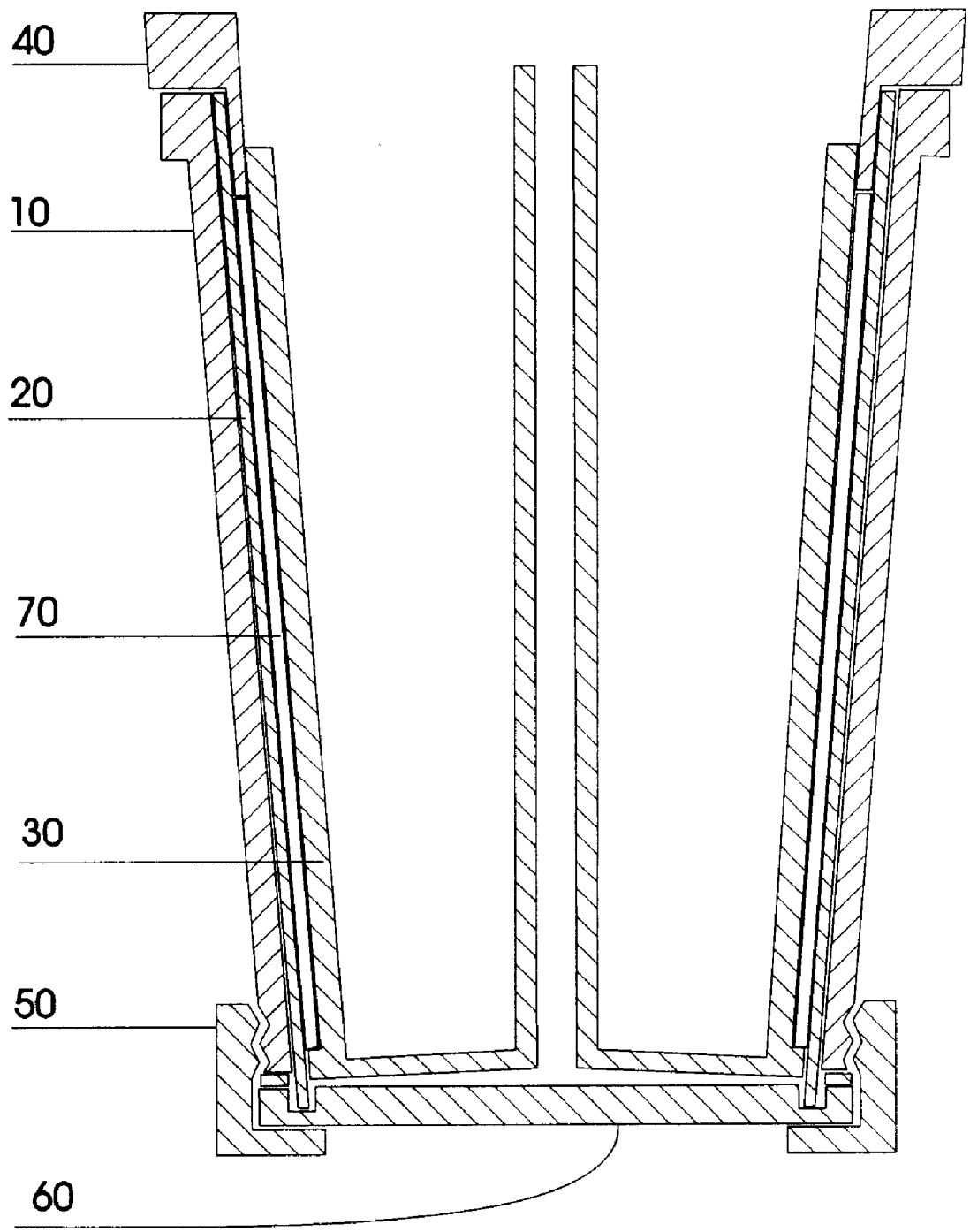
FIG. 2 is a cross-sectional view of the assembled gel casting apparatus in which a gel slab is enclosed.

Referring now to FIGS. 1 and 2, to prepare a gel slab by the present invention, disc member 60 is placed in cavity 53 of screw member 50 with bottom surface 62 facing rim 51 of screw member 50. Outer casting member 10 is threaded into screw member 50, which seals second opening 14 of outer casting member 10 by gasket 64 of disc member 60. Flexible sheet 20 lines along the interior wall of channel 15 of outer casting member 10 in such a way that top side 21 of the flexible sheet levels with wide end 11 of outer casting member 10, the flexible sheet is in intimate contact with the entire interior surface of channel 15 of outer casting member 10, left vertical side 23 and right vertical side 24 of the flexible sheet are in close contact but are not overlapped, and bottom side 22 of the flexible sheet extends into groove 63 of disc member 60. A cup-shaped cavity lined laterally by a flexible sheet is thus formed. Comb member 40 is placed at the opening of the cup-shaped cavity with teeth 41 in the cavity and flange 43 sitting on wide side 11 of outer casting member 10 to restrict the comb member from moving. A gelable solution of defined volume is poured into the cup-shaped cavity and inner casting member 30 is then inserted into the cavity to squeeze the solution into the interstice between the interior wall of the cup-shaped cavity and the exterior wall of inner casting member 30. When inner casting member 30 reaches disc member 60, base slot 32 is in close contact with the interior wall of the cup-shape cavity to form an interstice of hollow frustum of even thickness. Teeth 41 of comb member 40 thus extend in the gelable solution and are sandwiched between the top portion of wall 31 of inner casting member 30 and the mid-top portion of the interior wall of the cup-shaped cavity.

Referring now to FIGS. 2 and 3, after the gelable solution solidifies to form gel slab 70, comb member 40 is removed to leave first gel exposure 71 with a plurality of wells (not shown in the FIGS.) for sampling. Disc member 60 is also removed to leave second gel exposure 72 at the opposing side of first gel exposure 71. The remaining components form gel assembly 150 of frustum shape with first buffer chamber 110 on its wide end and second gel exposure 72 on its narrow end. First buffer chamber 110 comprises the top portion of the cup-shaped cavity and cavity 35 of inner casting member 30 (FIG. 1) with first gel exposure 71 at their junction. Gel assembly 150 is placed in second buffer chamber 120 containing a second buffer with second gel exposure 72 submerging in the buffer. A first buffer and movable electrode 130 are placed in first buffer chamber 110 with first gel exposure 71 covered by the buffer. Samples are loaded into the wells on first gel exposure 71 and electric current is applied onto gel slab 70 from the first gel exposure 71 and second gel exposure 72 by the two electrodes. After electrophoresis, gel slab 70 is separated from the casting components by slipping off outer casting member 10 from flexible sheet 20, peeling off flexible sheet 20 from gel slab 70, and removing gel slab 70 from inner casting member 40. Gel slab 70 is now ready for staining and analysis.

The combination of the hollow frustum casting mold and the flexible lining sheet forms the core of the invention and clearly distinguishes the present invention from the prior art described in the U.S. Pat. No. 4,729,823 and the art reported by J. Hejgaard. Hejgaard's art utilizes two hollow cylinders as the casting mold to prepare a hollow cylindrical gel slab. Although the hollow cylindrical gel slab might have advantages of large sample loading, uniform electric field, and better heat exchange, removal of the two cylinders from the gel slab is very difficult. Since the gel slab is cast in the interstice between the two concentric hollow cylinders, one has to pull one hollow cylinder away from the other in order to expose the gel slab for analysis. In most cases the gel slab is damaged during this operation, preventing the hollow cylindrical gel from practical use. The art described in the U.S. Pat. No. 4,729,823 uses two hollow frustums or cones as the casting mold to prepare a hollow frustum gel slab of which the sample loading end is many times wider than its opposing end. When a sample is migrating in the gel slab from the wide end to the narrow end, individual components are separated and concentrated. As point out in the patent, the art is used for preparative gel electrophoresis in which only one sample is separated in a single run and the individual components are collected from the end opposing to the sample loading end and the gel slab is not required to separate from its casting components. Multiple sample analysis cannot be performed in this design since the bands of different samples will crowd together once they approach the narrow end. Besides, slab gel electrophoresis for multiple samples requires the gel slab to be separated from its casting mold. The art described in U.S. Pat. No. 4,729,823 needs to pull one frustum away from another in order to expose the gel slab and the gel slab is thus damaged due to the same reason as for the hollow cylindrical gel slab. In the present invention, two hollow frustums are used to cast a gel slab the outer hollow frustum is lined with a flexible sheet and the gel slab is enclosed between the flexible sheet and the exterior wall of the inner frustum. After electrophoresis, the outer frustum is pulled away from the flexible sheet which protects the slab gel from damage during this operation. The flexible sheet is then removed from the gel slab by lifting, not pulling. Finally, the gel is removed from the inner frustum for staining and analysis. The last two steps are similar to the removal of plates from the conventional cassette-type gel slab and have no risk of gel damage.

In the present invention the gel slab is cast in the interstice of two hollow frustums and the gelable solution is squeezed into the interstice between the two hollow frustums by inserting the smaller frustum into the larger frustum containing the gelable solution. The process is so quick that vertical agarose gel slabs can be prepared at low temperature, another major advantage of the present invention. The conventional vertical gel slab and the gel slab described in the prior arts are prepared by adding gelable solution into the narrow interstice of a casting mold. As discussed in the BACKGROUND section, the addition is a relatively slow process and requires agarose solution to be hot to avoid solidifying during addition. The gel cools down in the interstice and shrinks. Gel shrinkage may cause gel break and generate void between the gel slab and the casting mold, resulting in band diffusion during electrophoresis. In the present invention, agarose solution can be cooled to about gelling temperature and poured into the outer frustum. The inner frustum is inserted in the outer frustum to squeeze the agarose solution into the interstice between the two frustums. This process takes only a few seconds and the agarose solution will not solidify during this operation. The present invention minimizes agarose gel shrinkage to the level that all the drawbacks from gel shrinkage are eliminated.

The present invention lowers the detection limit for agarose gel electrophoresis through sample concentration by isotachophoresis technique. This is specially important for the detection of low abundant components by agarose gel electrophoresis. As mentioned in the BACKGROUND section, isotachophoresis has never been applied to agarose gel electrophoresis since the conventional horizontal format requires the agarose gel slab to submerge in a single buffer while isotachophoresis requires the two opposing ends of the gel slab exposing to two different buffers. A new technique, called Slab Gel Isotacho/Electrophoresis, is also invented in the present invention. Referring to FIG. 3, leading buffer of high conductance is added in second buffer chamber 120, terminating buffer of low conductance is added in first buffer chamber 110, and gel slab 70 is prepared in the leading buffer. Isotachophoresis starts after samples are loaded and electric current is applied to the gel. After the samples are concentrated to narrow bands on the bottom of sample wells, electric current is discontinued and a few milliliters of the adjusting buffer of the highest conductance is added into the terminating buffer to adjust the conductance of the terminating buffer to the same level of the leading buffer. Electric current is applied to the gel again and the samples are separated by the principal of electrophoresis.

The present invention allows preparation of an agarose gel slab 3 to 5 times thinner than the conventional horizontal agarose gel slab. The thin gel slab provides many advantages compared to the thick gel slab of horizontal type. It overcomes band smear effect for the thick gel slab during blotting, generating sharp bands on blotting membrane; Higher voltage can be applied to the thin gel slab so that short electrophoresis time is obtained; The thin gel slab requires less material for preparation and is cost effective; The thin gel slab eliminates band broadening resulting from the uneven band movement in thick gels and increases resolution and efficiency.

The apparatus of the present invention can also be used to prepare polyacrylamide gel for protein analysis and is superior to any existing polyacrylamide gel system. It provides the simplest procedure to cast polyacrylamide gel and is convenient. Due to the circular geometry of the casting mold, thin wall can be maintained even large gels are prepared, so that better heat exchange is obtained to reduce band diffusion and higher voltage can be applied to shorten electrophoresis time. The circular geometry allows 3 times more samples to be analyzed compared to the conventional cassette-type vertical gel apparatus of the same size, resulting in high throughput analysis. Unlike the gel slab in the cassette-type vertical gel system, the gel slab prepared by the present invention has no vertical boundary so that an even electric field is generated across the gel slab and "band smiling effect" is eliminated.

It has been mentioned in the BACKGROUND section that large ultra-thin polyacrylamide gel slab is difficult to prepare and troublesome in removal of casting plates from the gel slab. These problems are solved in the present invention. Since the gelable solution is squeezed into the interstice of the two concentric hollow frustums, no air gap is generated during gel preparation. It is also easy to separate the gel slab from its casting mold. As described in the previous paragraphs, one side of the gel slab in the present invention is in contact with a flexible sheet the flexibility of the sheet allows one edge of the sheet being lifted apart from the gel slab without disturbing the remaining section. In this way the gel slab can be separated from the flexible sheet without damaging. Contrary to the present invention, the plates in the cassette-type slab gel are rigid. When one side of the plates is lifted apart from the gel slab, the whole gel slab is disturbed. The process becomes uncontrollable when a large cassette is used.

Many modifications can be made to the preferred embodiment. Referring to FIG. 1, screw member 50 and disc member 60 can be replaced by any means which detachablly seals second opening 14 of outer casting member 10. Left vertical side 23 and right vertical side 24 of flexible sheet 20 can be taped to form an intact hollow frustum before inserting into outer casting member 10 for lining. A hollow frustum sheet can also be constructed by other means, such as mold injection or fabrication from a thin flat sheet. In some cases a gel slab needs to stick on a membrane for post-electrophoresis treatment. This requirement can be fulfilled by replacing the flexible sheet with a membrane of hydrophilic surface. The gel slab will stick on the hydrophilic surface and be removed from the inner casting member together with the membrane.

The apparatus of the present invention may be constructed from a wide variety of materials such as plastic, glass, ceramic, or other materials as will be understood by those skilled in the art. The actual materials of construction are not intended as a limitation of the present invention. It is preferred, however, that flexible sheet 20, outer casting member 10, and inner casting member 30 be made of electrically non-conductive materials.

Many modifications and variations besides the embodiments specifically mentioned may be made in techniques and structures without departing substantially from the concept of the present invention. Accordingly, it should be clearly understood that the form of the invention described and illustrated herein is exemplary only, and is not intended as a limitation on the scope thereof.

What is claimed is:

1. A vertical gel electrophoresis apparatus comprising:

an outer casting member of hollow frustum having exterior and interior surfaces, opposing first and second ends, a first opening at said first end, a second opening at said second end, and a decreased diameter from said first opening to said second opening, said first opening being 0.1% to 40% larger than said second opening in diameter;

a flexible sheet lining detachably along and in intimate contact with said interior surface of said outer casting member and extending out of said second end of said outer casting member by a few millimeters, forming a sheet-lined channel, said sheet-lined channel having a first opening at said first end of said outer casting member, a second opening at said second end of said outer casting member, a sheet-lined interior surface, and a sheet extension portion at said second opening;

an inner casting member of cup shape having opposing first and second ends, a lateral wall of frustum shape with exterior and interior surfaces, a cavity at said first end, and a bottom at said second end, said exterior surface of said lateral wall having a decreased diameter from said first end to said second end and resembling said sheet-lined channel by shape but smaller than it by size, said inner casting member being positioned within said sheet-lined channel and being spaced apart from said interior surface of said sheet-lined channel by a spacing means to form an interstice therebetween;

a bottom member being detachably sealed onto said second opening of said sheet-lined channel by a sealing means;

a comb member having a circular base and a plurality of teeth locating around said circular base and extending perpendicularly to said circular base, said comb member being positioned at said first opening of said sheet-lined channel with said teeth extending into said interstice;

a gel medium being filled within said interstice, forming a gel layer when said gel medium solidifies.

2. The vertical gel electrophoresis apparatus of claim 1 wherein said sealing means comprises:

a male threaded portion on said exterior surface proximate to said second end of said outer casting member;

a disc member having opposing upper and lower surfaces, a diameter approximately equal to the diameter of said second end of said outer casting member, a concentric groove on said upper surface with an outer diameter approximately equal to the diameter of said second opening of said outer casting member;

a gasket ring having an outer diameter approximately equal to the diameter of said disc member and an inner diameter approximately equal to the outer diameter of said concentric groove of said disc member;

a screw member of hollow cylinder or frustum having opposing first and second openings, an lateral wall with interior and exterior surfaces, an inwardly projecting rim at said second opening, and a female threaded portion on said interior surface of said lateral wall, said first opening having a diameter approximately equal to the outer diameter of said second end of said outer casting member;

said disc member being located within said screw member with said lower surface of said disc member facing said rim of said screw member, said gasket ring being sandwiched between said upper surface of said disc member and said second end of said outer casting member to form a sealing means by threading said outer casting member into said screw member, said concentric groove of said disc member receiving said sheet extension portion of said sheet-lined channel.

3. The vertical gel electrophoresis apparatus of claim 1 wherein said sealing means is an adhesive tape.

4. The vertical gel electrophoresis apparatus of claim 1 wherein said spacing means comprises a plurality of protrusions along said second end of said inner casting member, said protrusions extending upwardly by a few millimeters from said second end and extending outwardly from said exterior surface of said lateral wall of said inner casting member by a distance approximately equal to the thickness of said interstice between said exterior surface of said lateral wall of said inner casting member and said interior surface of said sheet-lined channel.

5. The vertical gel electrophoresis apparatus of claim 1 wherein said bottom member is a cap having a top end, a bottom end with interior and exterior surfaces, a cavity of cylindrical or frustum shape at said top end, and a lateral wall with interior and exterior surfaces, wherein said cavity has an inner diameter approximately equal to the diameter of said second opening of said outer casting member and said top end of said bottom member has an outer diameter approximately equal to the outer diameter of said second end of said outer casting member;

wherein said sheet extension portion of said sheet-lined channel is positioned into said cavity of said bottom member and said second end of said outer casting member is detachably sealed onto said top end of said bottom member by a conventional means, such as by an adhesive tape.

6. The vertical gel electrophoresis apparatus of claim 1 wherein said inner casting member has an opening in the center of said bottom and a tubing structure extends longitudinally from said opening in a direction toward said top end.

7. The vertical gel electrophoresis apparatus of claim 1 wherein said flexible sheet has a shape of truncated hollow frustum.

8. The vertical gel electrophoresis apparatus of claim 1 wherein said flexible sheet is of truncated-fan shape having opposing convex and concave arc edges, and opposing side edges, wherein said convex arc edge has a length approximately equal to the circumference of said first opening of said outer casting member, said concave arc edge has a length equal to or smaller than the circumference of said second opening of said outer casting member, and the lengths of said side edges are equal to or larger than the length of said outer casting member.

9. The vertical gel electrophoresis apparatus of claim 1 wherein said flexible sheet has a thickness of 0.001 to 0.040 inch.

10. The vertical gel electrophoresis apparatus of claim 9 wherein said flexible sheet, said inner casting member, and said outer casting member are made of transparent plastic, such as polyester, polystyrene, polycarbonate, nylon, polyurethane, and their laminated products.

11. The vertical gel electrophoresis apparatus of claim 1 wherein said gel is made of noncross-linked polymers, or cross-linked polymers, or a mixture of both.

12. The vertical gel electrophoresis apparatus of claim 1 wherein said outer casting member, said inner casting member, and said flexible sheet are made of non-conductive materials, such as glass and plastic.

13. The vertical gel electrophoresis apparatus of claim 1 wherein said comb is removed to generate a first gel exposure with a plurality of wells and said bottom member is removed to generate a second gel exposure, said wells being used for sample loading, said first and said second gel exposures being used for conducting electric current during electrophoresis.

* * * * *